United States Patent
Raju et al.

(10) Patent No.: US 11,883,376 B2
(45) Date of Patent: *Jan. 30, 2024

(54) VIRAL INFECTION TREATMENT WITH 5-AMINOLEVULINIC ACID

(71) Applicants: Nadimpally Satyavarahala Raju, Hyderabad (IN); Venkata Satya Suresh Attili, Hyderabad (IN); Nadimpally Neha Varma, Hyderabad (IN); Steven Jerome Moore, Newtown, CT (US); Cullen Thomas Moore, Newtown, CT (US)

(72) Inventors: Nadimpally Satyavarahala Raju, Hyderabad (IN); Venkata Satya Suresh Attili, Hyderabad (IN); Nadimpally Neha Varma, Hyderabad (IN); Steven Jerome Moore, Newtown, CT (US); Cullen Thomas Moore, Newtown, CT (US)

(*) Notice: Subject to any disclaimer, the term of this patent is extended or adjusted under 35 U.S.C. 154(b) by 169 days.

This patent is subject to a terminal disclaimer.

(21) Appl. No.: 17/340,064

(22) Filed: Jun. 6, 2021

(65) Prior Publication Data

US 2021/0330622 A1   Oct. 28, 2021

Related U.S. Application Data

(62) Division of application No. 16/920,000, filed on Jul. 2, 2020, now Pat. No. 10,987,329.

(30) Foreign Application Priority Data

Apr. 22, 2020   (IN) .............................. 2020/41017237
Jun. 4, 2020   (IN) .............................. 2020/41026186

(51) Int. Cl.
*A61K 31/197*   (2006.01)
*A61K 36/23*   (2006.01)
*A61K 31/375*   (2006.01)
*A61K 31/315*   (2006.01)

(52) U.S. Cl.
CPC .......... *A61K 31/197* (2013.01); *A61K 31/315* (2013.01); *A61K 31/375* (2013.01); *A61K 36/23* (2013.01)

(58) Field of Classification Search
CPC ................................................... A61K 31/197
See application file for complete search history.

(56) References Cited

U.S. PATENT DOCUMENTS 5,192,788 A * 3/1993 Dixon .................... A61K 31/40
                                                              514/183

OTHER PUBLICATIONS

Lang et al. Journal of Photochemistry and Photobiology B: Biology, 2001, 65:29-34.*
Wen et al., Journal of Medicine Chemistry, 2007, 50(17): 4087-4095.*
Eickmann et al., Transfusion, 2018, 58(9): 2202-2207 (abstract).*

* cited by examiner

*Primary Examiner* — Rei Tsang Shiao

(57) ABSTRACT

A method for amelioration of, or prophylaxis against, a viral infection comprising administering to a patient in need of treatment a therapeutically effective amount of 5 aminolevulinic acid, optionally with at least one of cucumarin nano, zinc, vitamin C and methylene blue, and compositions thereof. Such compositions may be used for the treatment of coronavirus infections, including the SARS-CoV-2 virus, and/or rhinoviruses.

10 Claims, No Drawings

VIRAL INFECTION TREATMENT WITH 5-AMINOLEVULINIC ACID

CROSS REFERENCE TO RELATED APPLICATIONS

The present application claims priority to Indian Application Nos. 2020/41017237, filed Apr. 22, 2020, and 2020/41026186, filed Jun. 4, 2020, and is a divisional of U.S. patent application Ser. No. 17/132,602, filed Dec. 23, 2020, now U.S. Pat. No. 11,026,909, which is a divisional of U.S. application Ser. No. 16/920,000, filed Jul. 2, 2020, now U.S. Pat. No. 10,987,329.

TECHNICAL FIELD

The present invention relates to a method of treating viral infections in a subject in need thereof by administration, simultaneously or sequentially, of a therapeutically effective amount of 5-aminolevulinic acid with of at least one selected from the group of: an antioxidant, curcumin, zinc, and methylene blue. More particularly the present invention relates to a therapeutically effective combination of 5-aminolevulinic acid and curcumin, combination of 5-aminolevulinic acid and zinc, a combination of 5-aminolevulinic acid, curcumin and vitamin C, and a combination of 5-aminolevulinic acid, zinc and curcumin in the treatment of coronavirus infections. In another embodiment there is included a prescription formulation of 5-aminolevulinic acid and methylene blue and other such combinations in conjunction with a therapeutically effective dose of methylene blue directed to COVID-19. Such combinations are used for the treatment (including amelioration and protection) of coronaviruses infection, including Covid-19 infection, and common cold rhinoviruses.

BACKGROUND

Coronaviruses (CoV) are widespread viruses that cause a variety of illnesses ranging from the common cold to COVID-19. Human rhinoviruses (HRV) are a large family of viruses causing many common viral infections in humans. It is believed that both coronaviruses and rhinoviruses have the primary route of entry into humans via the upper respiratory tract, particularly the nose and mouth. Both coronaviruses and rhinoviruses are RNA viruses that cause disease in mammals. Rhinoviruses are non-enveloped single stranded RNA virus, and a member of the Piconavirus family. Rhinoviruses have a substantially spherical surface interrupted by protein spikes often referenced as fingers. Coronaviruses are lipid-bilayer enveloped positive-sense, single-stranded RNA virus, and a member of the Coronaviridae family. Coronaviruses have club-shaped spikes that project from their substantial spherical surface. Both coronaviruses (particularly, HCoV-OC43, HCoV-HKU1, HCoV-229E, and HCoV-NL63) and rhinoviruses (particularly, rhinovirus A, B and C) are causative agents of what is known as the common cold. Together these viruses are thought as accounting for up to 65% of all common colds. Respiratory syncytial virus ("RSV") and parinfluenza viruses are also believed to cause the common cold. Other viruses are also likely involved.

A new coronavirus, designated SARS-CoV-2, has ravaged the world since 2019. This virus first jumped into humans in Wahun, Hubei Province, China, and then quickly spread across the world. The SARS-CoV-2 virus has been associated with numerous maladies including some seen with common cold infections such as cough, sore throat, fever or chills, fatigue, headache, muscle or body aches, nausea, diarrhea, and congestion or runny nose. Other symptoms are largely distinct from the common cold, including shortness of breath, loss of taste or smell, and vomiting. The common cold also has been associated with sneezing which has not been reported as a common symptom of SARS-CoV-2 virus infection. In a pre-publication preprint by Nelde et al., *SArS-CoV-2 T-cell epitopes define heterologous and COVID-19-induced T-cell recognition*, Researchsquare.com, Jun. 17, 2020, the authors note that there is significant sequence alignment seen in SARS-CoV-2 derived peptide sequences and that of seasonal common cold human coronaviruses (HCoV-OC43, HCoV-229E, HCoV-N163, HCoV-HKU1). These authors suggest that heterologous immunity is seen between the common cold coronaviruses and SARS-CoV2. The group notes that cross-reactive SARS-CoV-2 T-cell epitopes revealed preexisting T-cell responses in 81% of persons unexposed to SARS-CoV-2.

COVID-19 represents a global public health concern and WHO has declared it a public health emergency. SARS-CoV-2 rapidly increased in spread in an epidemic scale since its first appearance in Wuhan, China, around December 2019. Among the most alarming symptoms that may be associated with SARS-CoV-2 infection is severe acute respiratory syndrome seen in a subpopulation, particularly those over 60 years of age and those suffering from underlying conditions such as Type II diabetes, chronic kidney disease, chronic obstructive pulmonary disease, immunocompromisation, a BMI of 30 or higher, heart conditions such as heart failure or coronary heart disease, and sickle cell disease. This respiratory syndrome is also referenced as "Novel coronavirus-induced pneumonia." Besides respiratory issues, it has been found that SARS-CoV-2 infection is associated with other serious life-threatening sequelae including blood clotting disorders that can lead to strokes, and with extreme inflammation that can lead to effects on multiple organ systems including the liver, the brain, and the kidney. The World Health Organization ("WHO") on Feb. 11, 2020 designated the disease caused by SARS-CoV-2 as Coronavirus Disease 2019 (2019nCoV or COVID-19). Unfortunately, it now appears that many persons who suffer from COVID-19, and yet survive, may face many years of medical care due to the damage caused by the virus. It is believed that nearly 50% of hospitalized patients recovering from COVID-19 complain of debilitating syndromes weeks after recovering from the virus, such as pains in the arms and legs, shortness of breath, being unable to sleep, and severe lethargy and anxiety.

SARS-CoV-2 has not less than ten open reading frames (ORFs). A major portion of this RNA (also forms ORF1a/b) is translated into two large polyproteins—pp1a and pp1ab, which are processed into 16 non-structural proteins (nsp1-nsp16), which form the viral replicas transcriptase complex that helps viral replication and transcription in the rough endoplasmic reticulum ("RER"). The remaining RNA (other ORFs) encode four main structural proteins: spike (S), envelope (E), nucleocapsid (N) and membrane (M) proteins, as well as several accessory proteins with unknown functions which are deemed to not participate in viral replication.

The current theory suggests that the novel coronavirus binds to the human ACE2 receptor through a spike protein and subsequent phagocytosis. While this remain the predominant theory, some data suggests that the coronavirus may also directly penetrate the human cell membrane by way of porphyrin. The present inventors have hypothesized that no one single mechanism of action is in play in regard to the detrimental effects of any coronavirus, and in particular with regard to SARS-CoV-2, and that to treat (by which it is meant proactively and preventively) the disease effectively, multiple therapeutic interventions should be undertaken to thwart the virus.

Once the virus infects—it gets recognized by antigen presentation cells (APC) and then recognized by virus-specific cytotoxic T lymphocytes (CTLs). However the reaction of innate immunity to this virus is quite varied. Besides HLA polymorphisms, gene polymorphisms of MBL (mannose-binding lectin) associated with antigen presentation are related to the risk of SARS-CoV-2 infection, which provide valuable clues for the prevention, treatment, and mechanism of COVID-19. Once the process of inflammation sets in and goes out of control "referred as cytokine storms" it leads to lung damage and ARDS—which is believed to be the main death cause of COVID-19. Immune effector cells during the cytokine storm release large amounts of pro-inflammatory cytokines (IFN-α, IFN-γ, IL-1β, IL-6, IL-12, IL-18, IL-33, TNF-α, TGFβ, etc.) and chemokines (CCL2, CCL3, CCL5, CXCL8, CXCL9, CXCL10, etc.).

Initial efforts to treat SARS-CoV-2 infection were directed to reduce RNAemia (viral load reduction) using broad-spectrum antiviral drugs like nucleoside analogues and HIV-protease inhibitors. Unfortunately, these (such as lopinavir-ritonavir) were not found to be very effective. Subsequently, pharmaceutical products, such as remdesivir, favipiravir, ribavirin and galidesivir), have been, or are still being, tested to determine if they were capable of interfering with the immune evasion of SARS-CoV-2. In particular, drugs thought capable of blocking the binding of S protein with ACE-2 were investigated as possibly useful in the treatment of COVID-19.

While vaccines and monoclonal antibodies are thought to be the long term solution for COVID-19, given the wide global spread of SARS-CoV-2, and the uncertainty as to the length of time any immunity by vaccination may last, further research into treatment is needed. Similarly, there remains a need for the treatment of other coronaviruses, in particular those associated with the common cold.

In a study employing conserved domain analysis, homology modeling, and molecular docking employing NCBI protein sequences it is found that ORF8 and surface glycoprotein could bind to porphyrin, respectively. At the same time, orf1ab, ORF10, and ORF3a proteins are seen to be able to coordinate to attack the heme on the 1-beta chain of hemoglobin to dissociate the iron to form porphyrin. Such a mechanism could be deemed to interfere with the normal heme anabolic pathway. In any case, such study suggests that there is a massive demand of porphyrins for viruses to survive. Therefore, the novel coronavirus is hypothesized to target hemoglobin and attack heme. It may be that SARS-CoV-2 virus directly interferes with the assembly of human hemoglobin.

Protoporphyrin IX has been suggested in vitro to show antiviral activities against a array of enveloped pathogenic viruses including SARS-CoV-2 (Lu et al. Broad-spectrum antivirals of protoporphyrins inhibt the entry of highly pathogenic emerging viruses, Pre-print bioRxiv May 9, 2020). Mice in vivo studies may suggest that with respect to certain viruses (but not Sars-CoV-2) that mean survival time and rate may be improved. Id. It has been advanced that proporphyrin IX inhibits infection in the early stage of virus entry through biophysically interacting with the hydrophobic lipids of enveloped virons, interfering with the formation of a negative curvature for fusion, and resulting in the blockage of the entry of enveloped viruses into host cells. Id. Studies before the rise of SARS-CoV-2 suggested porphyrins might be useful for the inactivation of viruses including those of the coronavirus varieties leading to the common cold.

5-ALA is known to be metabolized to protoporphyrin IX under certain conditions particularly in cancer cells. However, the rate of such metabolism from an exogenous source is not clear. It was therefore unknown to the present inventors as to whether 5-ALA could produce enough protoporphyrin IX to aid in the treatment of coronavirus infections, including that of the common cold and COVID-19. Certainly it was unclear in respect of COVID-19 whether 5-ALA could aid in the inactivation of the virus or reduce coagulation disorders given the need of metabolism.

The inventors realized that porphyrin is an important material for the synthesis of heme. The present inventors hypothesized that the SARS-CoV-2 virus leads to too much free iron in the body, by way of the virus competing with iron for the porphyrin. Free iron in the blood is known to trigger free radicals. Unfortunately such toxic oxidative iron when "disassociated" (released) may be causing numerous syndrome seen in COVID-19, for example:
  a. Damaged RBCs which may lead to tissue hypoxia. They may also lead to debris which acts as "Pro-thrombotic material" which can cause micro thrombi (which explain the atypical ARDS and partial Shunt like picture observed in the COVID patients on ventilator-supported by autopsy series). That is, it is hypothesized by the present inventors that the hunt of porphyrins by the virus may be associated with clotting.
  b. The free radical iron helps to increase cytokine damage to the lungs.

Iron supplementation might seem advantageous in treating COVID-19 patients due to the virus' interference with hemogloblin. However, the present inventors have found this not to be true. When SFC was added to 5 ALA, it was found that the iron bound to the porphyrin—there by reducing the availability of free porphyrin at the infection site. The observation that severe COVID-19 patients have excess blood and tissue levels of iron can explain the failure of SFC added to 5 ALA. The present inventors now recognize that treating COVID-19 patients with the iron is without substantial use as the patients have their iron stripped from their hemoglobin (rendering it abnormally nonfunctional). In such cases, ventilator intubation is futile, unless one is just hoping the patient's immune system will work its magic in time—as per few reports. While one might think iron chelators would work in accelerated healing in severe COVID patients, such drugs may be limited in use as being unable to reach the target site.

Methylene blue is known to reduce the ferric iron in hemoglobin to ferrous. The ferrous form is the form that allows oxygen carriage. A number of studies have surprisingly seen methemoglobemia in COVID-19 patents, albeit it is not known if this is caused by treatment protocols or the disease itself. Another well-recognized problem seen in some COVID-19 patients is coagulopathy and hyperviscosity which may be due fibrin changes. Methylene blue is known to disturb fibrin polymerization. It has been reported that inflammatory proteins produced during infection in COVID-19 make platelets "hyperactive" make them aggregate faster. In a preprint dated Jun. 23, 2020 (Zaid et al., *Platelets can contain SARS-CoV-2 RNA and are hyperactivated in COVID-19*, medRxiv.SARS-COV-2 RNA can be found in platelets. Such may be associated with the increased number of blood clots seen in COVID-19 patients.

Methylene blue has been reported to inhibit arachidonic acid metabolism in human platelets in vitro (Losche et al. *Methylene Blue Inhibits the Arachidonic Acid Metabolism in Human Blood Platelets*, Biomed. Biochim Acta. 198847(10-11):S100-5103). Methylene blue has also been shown to have antiviral properties. Thus the addition of methylene blue to a 5-ALA treatment may be employed to improve clinical outcome in COVID-19 cases, particularly moderate to severe cases, both due to its positive effect on methemoglobin, and its effect on red blood cells and platelets to reduce hyperviscosity, along with its antiviral activity. Thus COVID-19 patients may find particular advantage in a treatment comprising methylene blue alone, 5-ALA and methylene blue, or a combination of 5-ALA, methylene blue and at least one of: citric acid, cucumarin, and zinc.

In regard to all coronavirus infections, the present inventors have recognized that viral docking needs to be controlled during the disease state at the purported receptor site for the virus to reduce viral replication.

Studies on human coronaviruses OC43 and HKU1, causative agents of the common cold, found that both of these viruses employed sialoglycan-based receptors with 9-O-acetylated sialic acid (9-O—Ac-Sia) as a key component. Recent studies suggest that the S1 N Terminal Domains (S1-NTD) of the spike protein knobs of SARS-CoV-2 and SARS-CoV are hiding sites for recognizing and binding glycans containing sialic acid. It is hypothesized that this recognition may be important for infection allowing the virus to more accurately locate the ACE2 surface receptor. A recent article by Sorensen, Susrud, and Dalgeleish in QRB Discovery, after the studies reported below, suggests that ACE2 acts as the main receptor for SARS-CoV-2 with CLEC4M/DC-SIGN acts as a co-receptor in a similar manner as observed for HIV and its use of CD4 as the main receptor and the V3 Cys-Cys loop docking on the CCR5/CXR4 co-receptors. Thus the receptor binding domain (RBD) binds to the ACE2 receptor, and the NTD (n-terminal domain) binds to the ganglioside rich domain of the cellular plasma membrane. CLEC4M/DC-SIGN is sialic acid rich.

Curcumin is known to bind to sialic acid anchoring residues involved with the influenza virus (See Ou et al. Structure-activity relationship analysis of curcumin analogues on anti-influenza virus activity—looking at anti-influenza virus activity of curcumin analogues—(Ou et al. FEBS 280:22 (2013)). It has also been noted to reduce sialic acid levels and sialidase activity in mice with Ehrlich ascites tumors (Ozen, The Tohoku J. Experimental Medicine, September 2002: 221-7). Thus, the present inventors hypothesized that curcumin may be may be useful in coronavirus infections which appear to involve co-receptors, one of which is ganglioside rich. In the case of COVID-19, the curcumin was thought to be able to interfere with the ability of the virus to more efficiently dock to the ACE2 receptor.

Like 5-ALA, curcumin is a well-recognized antioxidant, also lending help in reducing free radical damage which is a sequelae of the covoronavirus infections. While curcumin has been shown to have many biological activities, its bioavailabilty has been a stumbling block for many years. Numerous absorption enhancers have been employed including piperine, black pepper, quercetin, ascorbic acid, and phosphatidyl choline. A leap in bioavailability has occurred in respect of nanoparticle milling and nanoparticle encapsulation.

Zinc has long been recognized as having a role in antiviral immunity (See, Read et al. Adv. Nutr 10: 696-710 (2019)) in respect of both coronaviruses and rhinoviruses through modulation of viral particle entry, fusion, replication, viral protein translation and further release for a number of viruses including those involved in respiratory system pathology. Zinc is also known to interfere with coronvirus RNA polymerase activity. At least one group has suggested that Zinc may also be useful in decreasing the activity of angiotensin-converting enzyme 2 in COVID-19 disease (See, Skalny et al., Zinc and Respiratory Tract Infections: Perspectives for COVID-19 (Review), Int. J. Mol Med. 2020 Apr. 14; 46(1)"17-26). The present inventors hypothesized that if zinc interfered with angiotensin-converting enzyme 2 that it might have synergistic effects with the curcumin in again interfering with efficient docking of the virus to the cells, improving the treatment of COVID-19 patients, and patients suffering from other coronavirus diseases.

Vitamin C, or ascorbic acid, has been indicated in a number of publications as affecting the immune system, for example the function of phagocytes, transformation of T lymphocytes and production of interferon. Vitamin C is one compound elicited as a potential target for SARS-CoV-2 by computational methods. (See, Wu et al., *Analysis of therapeutic targets for SARS-CoV-2 and discovery of potential drugs by computational methods*, Acta Phamaceutica Sinica B. Feb. 12, 2020; 10(5):776-788), It has also been suggested to increase cucumarin bioavailabilty.

On May 1, 2020 USFDA issued Emergency Use Authorization of Remdesivir for the treatment of suspected or laboratory-confirmed COVID-19 in adults and children hospitalized with severe disease. Remdesivir interferes with viral reproduction by being incorporated into the growing viral RNA strand, thereby shutting down the assembly process and hampering the virus's ability to make copies of itself. Remdesivir has been reported as reducing hospitalization time by approximately 30 percent. The drug has been priced in the United States for hospital patients with commercial insurance at $3120. Beyond Remdesivir, there is no approved treatment regimen for the Covid-19 infection as of date. However, several drug combinations, treatment regimens or methods of treatments are being employed, none of which is approved and have one more of the above mentioned limitations.

The inventors of the present surprisingly found that combination of 5 ALA, vitamin C and curcumin can have a significant impact on COVID-19 infection. The inventors anticipate such combination would to translate to other coronavirus infections, in particular those causing the common cold. The inventors have also recognized that improvement of treatment of coronavirus and rhinovirus infections may be had when such combination is used in conjunction with zinc. Furthermore, they propose COVID-19 treatments may be enhanced by a combination comprising at least 5-ALA and methylene blue, optionally with at least one of curcumin, vitamin C, and zinc.

SUMMARY OF THE INVENTION

Accordingly, the invention herein provides a number of 5-ALA therapeutic combinations advantageous for the treatment of coronavirus and/or rhinovirus infections. Such combinations comprise a therapeutic dose of 5-aminolevulinic acid or its pharmaceutically accepted salts/metabolites, along with at least one of: curcumin, vitamin C, zinc and methylene blue. A particular advantageous combination for the treatment of cornonaviruses and/or rhinoviruses comprises, a therapeutic dose of 5-aminolevulinic acid, curcumin, vitamin C and Zinc. A particular advantageous combination for the treatment of COVID-19 coronavirus comprises a therapeutic dose of 5-aminolevulinic acid, curcumin and vitamin C. A more particularly preferred embodiment for the treatment of COVID-19 comprises a therapeutic dose of 5-aminolevulinic acid, curcumin, vitamin C and Zinc. Any of such combinations may be combined with methylene blue to form a prescription product for the treatment of patient suffering from COVID-19, particularly moderate to severe form. The therapeutic combinations disclosed herein are effective in the treatment of coronavirus infections, particularly those causing the common cold and COVID-19, and rhinoviruses, that is, in the prophylaxis, early infection and mid & late infection phases.

Such combinations may significantly reduce the time over which the patient suffers from serious symptoms due to coronavirus and/or rhinovirus infection. Such combinations may also be used to significantly reduce serious complications of the infections. The therapeutic combinations as disclosed herein can further comprise other antivirals and micronutrient adjuvants. Prophylaxis from coronavirus and/or rhinovirus infection may be had by consumption of the same.

The present invention also provides compositions comprising therapeutic combination of 5-aminolevulinic acid or its pharmaceutically accepted salts/metabolites or the agents that shall eventually get converted to porphyrins after metabolism to raise the serum levels of porphyrins between 15-45 micro mol/liter, Vitamin C, curcumin and one or more pharmaceutically acceptable excipients and also provides process for preparing the same.

BRIEF DESCRIPTION OF THE INVENTION

One embodiment of the present invention is therapeutic combination of 5-aminolevulinic acid or its pharmaceutically accepted salts/metabolites, Vitamin C and curcumin. In another embodiment of the present invention there is provided a composition comprising 5-aminolevulinic acid or its pharmaceutically accepted salts/metabolites, Vitamin C and curcumin and one or more pharmaceutically acceptable excipients.

In an another embodiment of the present invention provides therapeutic combination of 5-aminolevulinic acid or its pharmaceutically accepted salts/metabolites, vitamin C and curcumin further comprising other antivirals and/or micronutrient adjuvants. In an another embodiment of the present invention there is provided a process for preparing a composition comprising 5-aminolevulinic acid or its pharmaceutically accepted salts/metabolites, vitamin C, curcumin and zinc and one or more pharmaceutically acceptable excipients.

In another embodiment of the present invention provides methods of treating coronavirus infections, including Covid-19. The method of treatment comprises the step(s) of administering a therapeutic combination of 5-aminolevulinic acid or its pharmaceutically accepted salts/metabolites, vitamin C and curcumin. The therapeutic combination can be administered as prophylactic treatment as well as to a patient in need thereof who is having early infection or mid and late infection phases. The therapeutic combination as disclosed herein advantageously achieves a therapeutic synergy in treating the Covid-19 in the patient/subject.

5 ALA is administered preferably as a solid as 5 ALA hydrochloride or 5 ALA phosphate although oil can be. The 5 ALA is administered in dosage of 1-1600 mg, more preferably 100 mg-1600 mg, yet more preferably 200 mg-1600 mg, or 300 mg-1600 mg in in single or divided doses of twice daily or thrice daily. In a preferred amount, ALA dosage is set to allow for serum levels of porphyrins between 15-45 micro mol/liter to be reached The dosage of 5-ALA is given based on weight of the patient/severity of infection.

Vitamin C is administrated in dosage of 1-1000 mg, more preferably 80 mg-1000 mg, and yet more preferably 500 mg-1000 mg in single or divided doses of twice daily or thrice daily. The dosage of Vitamin C is given based on weight of the patient/severity of infection.

Curcumin is administered in dosage of 1-1000 mg, more preferably 50 mg-1000 mg, and yet more preferably 100 mg-1000 mg in single or divided doses of twice daily or thrice daily. The dosage of Curcumin is given based on weight of the patient/severity of infection. Curcumin may preferably be administered in micronized or nanoform of curcumin for faster and more complete absorption.

Zinc is administered in a dosage of 5 mg-150 mg a day. More preferably 5-100 mg a day in single or divided doses. Zinc may in one embodiment be administered as zinc gluconate or zinc bis-glycinate.

In the treatment of COVID-19, methylene blue may be optionally added to such combinations in a dose of 1 mg/kg i.v. or orally at 1-30 mg/kg, more preferably 2.5-25 mg/kg, or 1-4500 mg, more preferably 50 mg-250 mg, in single or divided doses of twice daily or thrice daily. Methylene blue is available as an injectable and as an oral tablet. No suppository of such drug is known. It is herein suggested that treatment with methylene blue can be by way of suppository, allowing for treatment that allows the drug to be effectively absorbed without the need for intravenous or per os administration.

Administration of the compounds and compositions described herein can be effected by any method that enables delivery of the compounds to the site of action. These methods include, though are not limited to delivery via enteral routes (including oral, gastric or duodenal feeding tube, rectal suppository and rectal enema), parenteral routes (injection or infusion, including intraarterial, intracardiac, intradermal, intraduodenal, intramedullary, intramuscular, intraosseous, intraperitoneal, intrathecal, intravascular, intravenous, intravitreal, epidural and subcutaneous), inhalational, transdermal, transmucosal, sublingual, buccal and topical (including epicutaneous, dermal, enema, eye drops, ear drops, intranasal, vaginal) administration, although the most suitable route may depend upon for example the condition and disorder of the recipient. The compositions may be made into suppositories, lozenges, sachets. A novel methylene blue plus 5-ALA combination made be employed in a suppository or lozenge.

Antivirals may find particular synergistic effect with the described compositions in the treatment of COVID-19 and may be selected from at least one of: abacavir, lamivudine, zidovudine, didanosine, nevirapine, stavudine, lopinavir, ritonavir, tenofovir, emtricitabine, dolutegravir, raltegravir, cabotegravir, cobicistat, rilpivirine, favipiravir, remdesivir, efavirenz, atazanavir, elvitegravir, etravirine, maraviroc and its pharmaceutically acceptable salts or esters or prodrugs and combinations thereof. Particularly useful antivirals to provide synergic antiviral activity of such combinations include remdesivir, hydroxychloroquine, and chloroquine.

Anti-inflammatories may also find synergistic use in treating severe COVID-19 patients selected from at least one of carprofen, clecoxib, baricitinib, and dexamethasone and their pharmaceutically acceptable salts or esters or prodrugs and combinations thereof.

If venous or arterial thrombosis or clinical signs of clotting are shown, anticoagulants in severe COVID-19 may also be employed with such compositions such as enaxoaprin, warfarin, or heparin.

Micronutrient adjuvants as described herein are selected from the group comprising of micro minerals, antioxidants (such as Vitamin E, beta-carotene, selenium, coenzyme Q10), choline and vitamins. Micro minerals are selected from the, uric acid group consisting of cobalt, chromium, copper, iodine, potassium, calcium, manganese, selenium, zinc, and molybdenum and its pharmaceutically acceptable salts and combinations thereof.

The therapeutic combination according to the present invention is administrated for at least 14 days, specifically at least 10 days, more specifically for at least 7 days, and may have application over 2-7 days. Specifically the treatment period is selected depend on severity of virus infection.

The combination according to the present invention may be in the form of kit comprising 5-aminolevulinic acid or its pharmaceutically accepted salts/metabolites, Vitamin C and Curcumin or tablets or capsules or suspension or solution or injection dosage form.

The combination according to the present invention may be in the form of co-packing comprising 5-aminolevulinic acid or its pharmaceutically accepted salts/metabolites, Vitamin C and Curcumin or tablets or capsules form.

The tablet dosage form according to the present invention may be an immediate release or extended release form. Further the tablet dosage form may be monolayer or bi-layer or tri-layer tablet or layered tablets containing active drug in different coating layers. In a preferred embodiment the tablet is an orally disintegrable tablet.

In an embodiment of the present invention the dosage form may be pellets of 5-aminolevulinic acid or its pharmaceutically accepted salts/metabolites, Vitamin C, and curcumin filled in capsules or compressed into tablets.

The therapeutic combinations according to the present invention may comprise one or more pharmaceutically acceptable excipients.

One or more pharmaceutically acceptable excipients are advantageously selected from diluents, binders, disintegrants, lubricants, glidants, sweetening agents, flavoring agents and colorants and combinations thereof.

Diluents are inactive ingredients that are added to tablets and capsules in addition to the active drug. A good diluent must be inert, compatible with the other components of the composition, non-hygroscopic, relatively cheap, compatible, and preferably tasteless or pleasant tasting. Suitable diluents according to the present invention are selected from mannitol, micro crystalline cellulose, lactose, sucrose, glucose, sorbitol, starch and its derivatives, dibasic calcium phosphate and combinations thereof.

Binders are agents added to tablet/capsule/granule composition for binding with other substances to form granules and are selected from the group consisting of povidone, starch, potato starch, wheat starch, corn starch, hydroxypropyl methylcellulose, hydroxypropyl cellulose, hydroxyethyl cellulose, gelatin and combinations thereof.

Disintegrants are agents added to tablet/capsule composition to promote the breakup of the granules/tablet into the small fragments in an aqueous environment thereby increasing the available surface area and promoting a more rapid release of the drug substance. Suitable disintegrants according to the present invention are selected from Crospovidone, croscarmellose sodium, croscarmellose calcium, starch and its derivatives, sodium starch glycolate, polacrilin sodium, low substituted hydroxypropyl cellulose, silicified microcrystalline cellulose and combinations thereof.

Lubricants are agents which prevent ingredients from clumping together and from sticking to the tablet punches or capsule filling machine. Lubricants also ensure that tablet formation and ejection can occur with low friction between the solid and die wall. Suitable lubricants according to the present invention are selected from calcium stearate, magnesium stearate, stearic acid, and talc and combinations thereof.

Glidants are agents these are used to promote powder flow by reducing inter particle friction and cohesion. Suitable glidants according to the present invention are selected from colloidal silicon dioxide, talc and starch.

Sweetening agents are substances that sweeten medications, food, beverages etc., and suitable sweeteners according to the present invention are selected from aspartame, sucralose, xylitol, sweefil, sweegel, saccharine, sorbitol, maltitol, and combinations thereof.

Flavoring agents are substances added to medicines and foods to improve the quality of taste. Suitable flavoring agents according to the present invention may be selected from vanilla flavor, forest fruit flavor, fruit essences, peppermint oil, spear mint oil, clove oil, orange oil, anise oil and combinations thereof.

Colorants are agents which gives a special character or distinguishing quality to the pharmaceutical dosage forms. Coloring may be required to increase the aesthetic appearance or identification of a particular composition. Suitable colorants according to the present invention may be selected from indigo carmine lake, iron oxide yellow and iron oxide red and combinations thereof.

The compositions are prepared by techniques known by the skilled person in the art like direct compression or wet granulation or dry granulation. The compositions may be in form of powder and may be filled in capsules or sachets or may be compressed into tablets of immediate release or orally disintegrating or modified release.

Direct compression technique generally involves blending all ingredients in a blender for suitable time till to achieve blend uniformity and compressing into tablets of suitable size and shape.

Wet granulation technique generally involves utilization of solvents for preparation of granules. This process generally has the steps of mixing active ingredient with diluent, optionally disintegrant, granulating this mixture either by aqueous or non-aqueous granulation, drying the granulate, optionality sieving dried granules and blending dried granules with optionally further diluent, disintegrant, optionally sweetening agent, optionally flavoring agent, optionally colorant and lubricated with lubricant. Suitable solvents used according to the present invention for preparation of wet granulation are selected from water, isopropyl alcohol, methylene chloride and combinations thereof.

Dry granulation is another technique which doesn't use any solvents for preparation of granules. This process generally has the steps of mixing active ingredient with diluent, optionally disintegrant, optionally lubricant, optionally glidant, slugging and de-slugging and blending with optionally diluent, optionally disintegrant, optionally lubricant, optionally glidant, optionally sweetening agent, optionally flavoring agent, optionally colorant.

Release modifying agents are used to modify the drug release from the dosage form. Suitable release modifying agents may be selected from hydroxypropyl methylcellulose, hydroxyl propyl cellulose, ethyl cellulose, methyl cellulose, carboxy propyl methyl cellulose, polyethylene oxide, xanthan gum, guar gum, Methacrylates, polyvinyl pyrrolidone, polyvinyl chloride, polypropylene and gelatin.

EXAMPLES

The present invention is further defined in the following examples. It should be understood that these examples, while indicating preferred embodiments of the invention are given by way of illustration only. From the above discussion and these examples, one skilled in the art can ascertain the essential characteristics of this invention, and without departing from the spirit and scope thereof, can make various changes and modifications of the invention to adapt it to various uses and condition.

The invention is illustrated by the following non limiting examples:

Example 1

Tablet Embodiment 1

| Ingredient | mg/tablet |
| --- | --- |
| 5-aminolevulinic acid or its salt | 300 mg |
| Curcumin | 100 mg |
| Vitamin C | 40 mg |
| Microcrystalline cellulose | 240 mg |
| Starch corn | 60 mg |
| Croscarmellose sodium | 20 mg |
| Magnesium stearate | 10 mg |
| Total | 770 mg |
| Film coating | 15 mg |
| Total tablet weight | 785 mg |

Example 2

Tablet Embodiment 2

| Ingredient | mg/tablet |
| --- | --- |
| 5-aminolevulinic acid or its salt | 300 mg |
| Curcumin | 100 mg |
| Vitamin C | 40 mg |
| Zinc Gluconate | 50 mg |
| Microcrystalline cellulose | 210 mg |
| Starch corn | 40 mg |
| Croscarmellose sodium | 20 mg |
| Magnesium stearate | 10 mg |
| Total | 770 mg |
| Film coating | 15 mg |
| Total tablet weight | 785 mg |

Manufacturing Process:

Sift all the ingredients, blend 5-aminolevulinic acid or its salt, Curcumin, Vitamin C, with or without Zinc. Microcrystalline cellulose, Starch corn and Croscarmellose sodium in a blender for 20 minutes and the blend is lubricated by adding magnesium stearate to the blender and blend for 5 minutes. Finally compress the blend into tablets and film coated the compressed tablets.

Example 3

Multilayer Tablet Embodiment 3

| Ingredient | mg/tablet |
| --- | --- |
| Layer 1 | |
| 5-aminolevulinic acid or its salt | 300 mg |
| Microcrystalline cellulose | 150 mg |
| Povidone | 10 mg |
| Sodium starch glycolate | 10 mg |
| Purifier water | q.s |
| Magnesium stearate | 5 mg |
| Layer 1 tablet weight | 475 mg |
| Layer 2 | |
| Curcumin | 100 mg |
| Starch corn | 60 mg |
| Sodium starch glycolate | 10 mg |
| Magnesium stearate | 5 mg |
| Layer 2 tablet weight | 175 mg |
| Layer 3 | |
| Vitamin C | 40 mg |
| Microcrystalline cellulose | 150 mg |
| Sodium starch glycolate | 10 mg |
| Magnesium stearate | 5 mg |
| Layer 3 tablet weight | 205 mg |
| Total | 855 mg |
| Film coating | 25 mg |
| Total tablet weight | 880 mg |

Manufacturing Process:

Layer 1:

Sift all the ingredients, blend 5-aminolevulinic acid or its salt, Microcrystalline cellulose, Sodium starch glycolate for 10 minutes; dissolve povidone in purified water and make binder solution; add slowly binder solution to the blend to form granules; dried the granules; loaded the granules into blender and add magnesium stearate to the blend and blend for 5 minutes.

Layer 2:

Sift all the ingredients, blend curcumin, Starch corn, and Sodium starch glycolate in a blender for 15 minutes and the blend is lubricated by adding magnesium stearate to the blender and blend for 5 minutes.

Layer 3:

Sift all the ingredients, blend Vitamin C, Microcrystalline cellulose, Sodium starch glycolate for 10 minutes; and the blend is lubricated by adding magnesium stearate to the blender and blend for 5 minutes.

Compress: Compress Layer 1, Layer 2 and Layer 3 blends into trilayer tablets.

Coating: Trilayer tablets coated with film coating.

Example 4

Sachet Embodiment

| Ingredient | mg/tablet |
| --- | --- |
| 5-aminolevulinic acid or its salt | 300 mg |
| Curcumin | 100 mg |

-continued

| Ingredient | mg/tablet |
| --- | --- |
| Vitamin C | 40 mg |
| Mannitol | 200 mg |
| Sorbitol | 50 mg |
| Fruit flavor | 10 mg |
| Total | 700 mg |

Manufacturing Process:

Sift all the ingredients, blend 5-aminolevulinic acid or its salt, Curcumin, Vitamin C, Mannitol, Sorbitol and Fruit flavor in a blender for 20 minutes and the blend is filled in sachets.

Example 5

Lozenge Embodiment

| Ingredient | mg/tablet |
| --- | --- |
| 5-aminolevulinic acid or its salt | 300 mg |
| Curcumin | 100 mg |
| Zinc Gluconate | 13.3 mg |
| Vitamin C | 40 mg |
| Acesulfame Potassium | 182.7 mg |
| Glycine | 50 mg |
| Isomalt | 7 mg |
| Fruit flavor | 7 mg |
| Total | 700 mg |

Example 6

15 SARS-CoV-2 hospitalized patients consume 200 mg 2-3 times daily 5-ALA phosphate, over 5-14 days, along with cucumarin nano 100 mg for 7-14 days, and vitamin C 80 mg-1000 mg over 7-14 days. Such treated cohort is otherwise treated with standard care for COVID-19 patients. The control cohort comprises 20 hospitalized patients receiving the same standard care but without consumption of 5-ALA, nano-cucumarin, or Vitamin C. Two patients in the control cohort develop the need for ICU admission, while none of the treated cohort advance to ICU. Total stay time in the hospital is reduced from a mean of 9.40±1.029 days to 7.07±0.67. Mean erythrocyte sedimentation rate ("ESR"), which is inverse to blood viscosity, is seen to be reduced from 23.35±8.419 in control to 16.33±3.90 in treatment group. Better five day viral clearance by nasal swab is seen in the treatment cohort (60%) versus control control (35%). Less disseminated intravascular coagulation is noted in the treatment cohort.

Example 7

Persons inflicted with a coronavirus infections are given at treatment of a daily dose of 300 mg-1600 mg 5-ALA phosphate, Vitamin C 80 mg-1000 mg, cucumarin nano 100-1000 mg, and zinc in a total of 5 mg-100 mg as zinc gluconate and/or zinc bis-glycinate. Such are provided in a single or divided doses of twice daily or thrice daily.

Example 8

Persons seeking prophylaxis against coronavirus infections are given at treatment of a daily dose of 300 mg-1600 mg 5-ALA phosphate, Vitamin C 80 mg-1000 mg, 100-1000 mg cucumarin nano, and zinc in a total of 5 mg-100 mg as zinc gluconate and/or zinc bis-glycinate. Such are provided in a single or divided doses of twice daily or thrice daily.

Example 9

Persons seeking prophylaxis against, and/or amelioration of coronavirus infections, are given at treatment of a daily dose of 300 mg-1600 mg 5-ALA phosphate, Vitamin C 80 mg-1000 mg, 100-1000 mg cucumarin nano, and zinc in a total of 5 mg-100 mg as zinc gluconate and/or zinc bis-glycinate. Such are provided in a single or divided doses of twice daily or thrice daily.

Example 10

Persons suffering from moderate or severe COVID-19 are given treatment with a dose of 300 mg-1600 mg 5-ALA phosphate with at least one of Vitamin C 80 mg-1000 mg, 100-1000 mg cucumarin nano, zinc in a total of 5 mg-100 mg as zinc gluconate and/or zinc bis-glycinate, and methylene blue in a dose of 50 mg-250 mg. Such are provided in a single or divided doses of twice daily or thrice daily.

Example 1

Tablet Embodiment 4

| Ingredient | mg/tablet |
| --- | --- |
| 5-aminolevulinic acid or its salt | 300 mg |
| Curcumin | 100 mg |
| Vitamin C | 40 mg |
| Zinc Gluconate | 50 mg |
| Metthlene Blue | 50 mg |
| Microcrystalline cellulose | 160 mg |
| Starch corn | 40 mg |
| Croscarmellose sodium | 20 mg |
| Magnesium stearate | 10 mg |
| Total | 770 mg |

Example 12

Suppository Embodiment

Persons suffering from moderate or severe COVID-19 are given treatment with a suppository containing:

| Ingredient | mg/tablet |
| --- | --- |
| 5-aminolevulinic acid or its salt | 300 mg |
| Methylene blue | 100 mg |
| Theobroma Oil | 1600 mg |

The suppositories are molded so to have one end tapered.

The invention claimed is:

1. A method for amelioriation of a viral infection comprising administering to a patient in need of treatment a therapeutically effective amount of 5-aminolevulinic acid, or pharmaceutically acceptable salt thereof.

2. The method of claim 1 wherein the viral infection is an infection by SARS-CoV-2.

3. The method of claim 1 wherein the viral infection is associated with the common cold.

4. The method of claim 1 wherein the therapeutically effective amount of 5-aminolevulinic acid is 100 mg-1600 mg provided in a single or divided doses of twice daily or thrice daily.

5. The method of claim 1 wherein the therapeutically effective amount of 5-aminolevulinic acid is 200 mg-1600 mg provided in a single or divided doses of twice daily or thrice daily.

6. The method of claim 1 wherein the therapeutically effective amount of 5-aminolevulinic acid is 300 mg-1600 mg provided in a single or divided doses of twice daily or thrice daily.

7. A pharmaceutical composition comprising 5-aminolevulinic acid or pharmaceutically acceptable salt thereof, and a non-iron micronutrient, each present in therapeutically effective amounts, in an admixture with pharmaceutically acceptable excipient.

8. The composition of claim 7 wherein the therapeutically effective amount of 5 aminolevulinic acid is 100 mg-1600 mg provided in a single or divided doses of twice daily or thrice daily.

9. The composition of claim 7 wherein the therapeutically effective amount of 5 aminolevulinic acid is 200 mg-1600 mg provided in a single or divided doses of twice daily or thrice daily.

10. The composition of claim 7 wherein the therapeutically effective amount of 5-aminolevulinic acid is 300 mg-1600 mg provided in a single or divided doses of twice daily or thrice daily.

* * * * *